United States Patent
Dinamarca et al.

(10) Patent No.: US 12,150,449 B2
(45) Date of Patent: Nov. 26, 2024

(54) **EXTRACT OF BACTERIAL ORIGIN PRODUCED BY THE BACTERIA *KOCURIA MARINA* SP AND USE THEREOF TO GENERATE POLYMER STRUCTURES WITH BIOACTIVE SURFACES ABLE TO INHIBIT MICROBIAL BIOFILM FORMATION**

(71) Applicants: FUNDACION COPEC UNIVERSIDAD CATOLICA, Santiago (CL); UNIVERSIDAD DE VALPARAISO, Valparaiso (CL)

(72) Inventors: Alejandro Dinamarca, Valparaiso (CL); Claudia Ibacache, Valparaiso (CL); Juan Ojeda, Valparaiso (CL); Natalia Romo, Valparaiso (CL)

(*) Notice: Subject to any disclaimer, the term of this patent is extended or adjusted under 35 U.S.C. 154(b) by 993 days.

(21) Appl. No.: 17/056,183

(22) PCT Filed: Dec. 28, 2018

(86) PCT No.: PCT/CL2018/050159
§ 371 (c)(1),
(2) Date: Nov. 17, 2020

(87) PCT Pub. No.: WO2019/126902
PCT Pub. Date: Jul. 4, 2019

(65) Prior Publication Data
US 2021/0289792 A1    Sep. 23, 2021

(30) Foreign Application Priority Data
Dec. 28, 2017   (CL) .................................. 3446-2017

(51) Int. Cl.
| | | |
|---|---|---|
| A61K 36/00 | (2006.01) |
| A01N 25/10 | (2006.01) |
| A01N 25/12 | (2006.01) |
| A01N 63/20 | (2020.01) |
| A61L 29/00 | (2006.01) |
| A61L 29/16 | (2006.01) |
| C12P 7/6409 | (2022.01) |

(52) U.S. Cl.
CPC ............ *A01N 63/20* (2020.01); *A01N 25/10* (2013.01); *A01N 25/12* (2013.01); *A61L 29/005* (2013.01); *A61L 29/16* (2013.01); *C12P 7/6409* (2013.01)

(58) Field of Classification Search
None
See application file for complete search history.

(56) References Cited

U.S. PATENT DOCUMENTS

| 9,629,882 B2 | 4/2017 | Dinamarca Tapia et al. |
| 2008/0095871 A1 | 4/2008 | Riquelme Salamanca et al. |

FOREIGN PATENT DOCUMENTS

| EP | 2 716 749 | 4/2014 |
| WO | 2005/109960 | 11/2005 |

OTHER PUBLICATIONS

Kumar et al. (2017) Current Trends in Biotechnology and Pharmacy, vol. 11 (3): 300-308. (Year: 2017).*
Kumar, et al., "Optimiaztion for Enhanced Production of Antibacterial Metabolites by Marine Actinomycetes *Kocuria* sp. strain rsk4", Current Trends in Biotecnhology and Pharmacy, vol. 11(3), Jul. 2017, pp. 300-308.
Undabarrena, et al., "Exploring the Diversity and Antimicrobial Potential of Marine Actinobacteria from the Comau Fjord in Northern Patagonia, Chile", Frontiers in Microbiology, vol. 7, article 1135, Jul. 19, 2016, 16 pages.
Linares-Otoya, et al., "Diversity and Antimicrobial Potential of Predatory Bacteria from the Peruvian Coastline", Marine Drugs, 15, 308, Oct. 2017, 14 pages.
Ballav, et al., "Halophilic and halotolerant actinomycetes from a marine saltern of Goa, India Producing anti-bacterial metabolites", Journal of Bioscience and Bioengineering, vol. 119, No. 3, Mar. 2015, pp. 323-330, available online Oct. 22, 2014.
Kavitha, et al., "Biological Significance of Marine Actinobacteria of East Coast of Andhra Pradesh, India", Frontiers in Microbiology, vol. 8, article 1201, Jul. 6, 2017, 16 pages.
Schinke, et al., "Antibacterial Compounds from Marine Bacteria, 2010-2015", Journal of Natural Products, vol. 80, No. 4, Mar. 31, 2017, pp. 1215-1228.
International Search Report issued in International Application No. PCT/CL2018/050159, Apr. 10, 2019, 3 pages.

* cited by examiner

*Primary Examiner* — Russell G Fiebig
(74) *Attorney, Agent, or Firm* — HSML P.C.

(57) ABSTRACT

The invention relates to a method for obtaining a bacterial extract produced by the bacteria *Kocuria marina* sp., which prevents biofilm formation, to said extract, and to the use thereof for incorporation into natural or synthetic polymers intended to form structures with active surfaces for preventing microbial biofilm formation, whether for biomedical uses, including clinical uses, industrial uses, or even domestic uses.

7 Claims, 6 Drawing Sheets

EXTRACT OF BACTERIAL ORIGIN PRODUCED BY THE BACTERIA *KOCURIA MARINA* SP AND USE THEREOF TO GENERATE POLYMER STRUCTURES WITH BIOACTIVE SURFACES ABLE TO INHIBIT MICROBIAL BIOFILM FORMATION

TECHNICAL FIELD

The invention aims at a method to obtain a bacterial extract that prevents biofilm formation, to said extract and to the use thereof for incorporation into natural or synthetic polymers intended to form structures with active surfaces for preventing microbial biofilm formation, whether for biomedical uses, including clinical uses, such as for industrial uses or even domestic uses.

BACKGROUND OF THE INVENTION

Microbial biofilms present on surfaces are a cross-cutting problem that ranges from human health, the food industry, the pharmaceutical industry to the fishing industry, aquaculture, air conditioning systems, domestic pipes, and marine, lake, and industrial facilities in general. The problem of microbial biofilm formation is due to the fact that certain microorganisms can adhere to living organic surfaces or inert surfaces immersed in aqueous or liquid media where they find favorable conditions for their growth and dissemination, structuring a protected environment where nutrients are concentrated, relationships can be established with other microorganisms and where antimicrobial agents (antibiotics, metals, alcohols, and others) cannot access, which helps explain increased resistance. Microbial biofilms can be harmful to human health and different productive activities. The damage is associated with the fact that pathogenic bacteria can spread from colonized surfaces to other parts such as organs and tissues of an individual, in turn, bacteria existing in different environments can also produce physical modifications on colonized surfaces (damage by degradation or corrosion) generating an increase in the concentration of microorganisms and loss of infrastructure, so it is relevant to control the microbial biofilm formation. Control of pollution by microorganisms and specifically the biofilm formation on surfaces in aqueous environments is a problem that concerns all technical fields in which there are surfaces in contact with non-sterile aqueous media. These technical fields range from applications as sophisticated as devices for medical use such as catheters, implants, valves, probes, or other elements in biomedicine that are in contact with tissues or body fluids—which can become contaminated with bacteria generating foci of infection and the subsequent appearance of pathologies—less sophisticated such as pipes, ventilation ducts, filters, submerged surfaces of marine structures, pipes, hoses, reactors, fish tanks, fish farming tanks, industrial devices, etc. from industries as diverse as food, tourism, energy industries, mining, shipping, aquaculture, and others.

Depending on the technical field, there are a variety of solutions to address this problem. In biomedical uses, antibiotics have even been used to impregnate urinary catheters to prevent urinary and systemic infections. While that prevents bacterial biofilms on submerged structures in seawater environment traditionally they have been used paints or coatings formulated with heavy metals or other toxic biocidal compounds and aggressive environment.

In this context, there is a latent need for compounds that are capable of inhibiting biofilm formation on surfaces in contact with aqueous environments, and that at the same time are harmless to the environment and living beings, that do not contain antibiotics, and that they are safe to handle, and ideally, they can even be used in clinical uses or be in contact with food, without prejudice to the health of the end-user or consumer.

In this context, the inventors have developed a new bacterial extract produced in a liquid-solid two-phase culture using the bacterium of marine origin *Kocuria* sp, where the extracellular extract produced, or the same bacterium can be suitably incorporated into polymeric matrices to form active surfaces capable of inhibiting microbial biofilm formation. In particular, the inventors worked with the strain obtained by themselves *Kocuria* sp MM1A2AB, isolated from the marine environment and which degrades aromatic hydrocarbons, with the deposit record RGM2414 in the Chilean Collection of Microbial Genetic Resources (CChRGM), however, the extract with the physical and biological properties detailed in the present invention, can be obtained according to the described method that uses any bacterial strain of marine origin of the type and characteristics of the *Kocuria* sp strain of the present invention.

This extract can be suitably mixed with polymers of natural or synthetic origin, which when polymerizing and solidifying, generate structures whose surfaces are active for the inhibition microbial biofilm formation. Without limiting wanting by theory, it is postulated that this extract produced by the strain of the invention has the ability to modify gene transcription producing changes that affect the expression of genes associated with biofilm formation and bacterial virulence as by, for example, those bacterial communication systems known as Quorum Sensing (QS), without other mechanisms of the cellular stress type being also affected and/or activated.

In the prior state of the art, we find some documents with a close approach to the present invention, however, none of them anticipates obtaining an extract from the bacterium of marine origin *Kocuria* sp, which inhibits biofilm formation when successfully incorporated into different polymeric matrices.

On the one hand, the same inventors protected in Chile and the USA (under the patents; CL 50,735 and U.S. Pat. No. 9,629,882 (B2)) a process to produce a bacterial extract with surfactant properties useful for aquaculture that inhibits the virulence and biofilm formation of fish pathogenic bacteria; *Vibrio anguillarum* and *Aeromonas saimonicida* using the Gram-negative bacterium *Cobetia* strain MM1 IDA2H-1 deposited in the Spanish Collection of Type Cultures (CECT) with the registration: N ° 7764. In this same line of development, the University of Antofagasta has an anti-macro and micro fouling protected in patent CL47339 (US2008095871 (A1)) that comprises an extracellular extract of marine bacteria, in this case of the Gram-negative proteobacterium *Alteromonas* sp.

Bacteria of the genus *Kocuria* differ from *Cobetia* and *Alteromonas* in that they are Gram-positive bacteria that are part of the non-bacterial phylum Actinobacteria, *Cobetia* and *Alteromonas* are Gram-negative bacteria of the phylum Proteobacteria. This indicates a taxonomic difference and a great phylogenetic distance between *Kocuria* and the alluded genera. For those skilled in the art, it will be evident that it is not possible to anticipate that the extract produced by a bacterial species or genus, has a composition and physical, chemical, and biological properties like the extracts produced by bacteria of other genera, such as *Cobetia* and *Alteromonas*. Even less considering the cultivation methods or production processes of the extracts, as well as the possibility of adequately integrating the extracts generated in polymers of synthetic or natural origin to form bio-active structures, since the ability to form stable emulsions with polymers does not it is an obvious or widespread property of biological extracts. Therefore, it was not possible, until the present invention, to anticipate the physical and chemical properties that allow the generation of structures with anti-biofilm surfaces that are described here.

Figure 1:
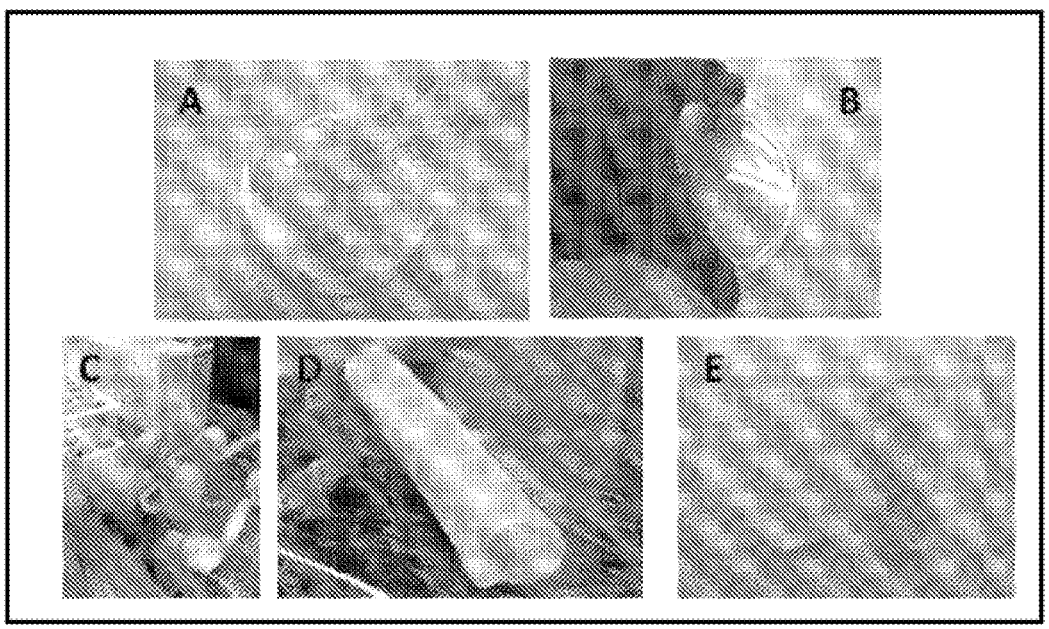
FIG. 1. The cell-free supernatant bacterial extract of the *Kocuria* sp bacterium called ETA can be integrated into commercial polymers to create flexible solid structures, the design of which will depend on the template used. The ETA supernatant from the culture of the *Kocuria* sp. Cell-free and lyophilized is mixed in a proportion of 0.01% to 0.1% (w/vol.) with liquid silicone-free of antifungal or antimicrobial agents or other resins or polymers (A). The mixture obtained was put into molds to structure its polymerization and subsequent solidification for 24 to 72 hours (B) and (C). By integrating ETA to polymers such as silicone, it is possible to generate tubular (D) and flat (E) structures.

FIG. 2. Structures with ETA do not form microbial biofilms. By incorporating the ETA into the silicone, it was possible to generate a structure that, when exposed to microorganisms, does not generate biofilm formation. Control silicone structures that do not contain ETA show the crystal violet coloration due to biofilm formation (control), while silicone structures with 0.1% (w/vol.) remain clean without forming microbial biofilms.

FIG. 3. Evaluation tests of bioactive polymeric structures in urine. To evaluate the biofilm inhibition capacity of uropathogenic bacteria, bioactive structures formulated in silicone as a polymerizing agent and an inorganic agent with recognized antimicrobial activity (for example, silver) or ETA (A) were manufactured. These structures were immersed in sterile human urine (decanted and filtered at 0.22 um) containing *Escherichia coli* bacteria cells for 1 to 10 days (B). The structures were finally evaluated for biofilm formation and bacterial viability at 10 days. Figure (C) shows a silicone-only catheter at 10 days stained due to biofilm formation and Figure (D) shows a silicone+ETA catheter, with substantially less biofilm formation evidenced by less staining.

FIG. 4. Viability in the urine of *Escherichia coli* bacteria cells exposed to polymeric structures, silicone-only control (A), or bio-active structures made with ETA (B) or with an inorganic compound with recognized antimicrobial activity: Ag (C). All conditions are evaluated at time 0 (TO), 8 hours (T8), 16 hours (T16), 24 hours (T24). The evaluation was performed by microscopy epifluorescence for which the liquid samples obtained from each condition (100 ul) were stained using Live/Dead Cell Double Staining Kit (Sigma-Aldrich Co., USA) containing dyes Calcein-AM and Propidium iodide the which allow differentiating respectively living bacteria in fluorescent green color (excitation: 490 nm, emission: 515 nm) and dead bacteria in fluorescent red color (excitation: 535 nm, emission: 617 nm). An epifluorescence microscope (Leica DM5000 B) was used for this. In light gray, the results are highlighted where the proportion of viable cells is higher than the dead cells (exceeds the reference value 1) and dark gray where the dead cells are in greater quantity (lower than the reference value 1). The cut-off value for the ratio of live and dead bacteria in equality corresponds to 1.

FIG. 5. Evaluation test of different types of bio-active coatings made based on different resins and ETA. The figure schematizes the test developed where slides were covered on their surfaces with millimeter films (sheets) of the respective coating containing silicone alone (control) or with silicone-ETA 0.01%-0.1% (w/vol) (invention). The slides containing the different coatings were sterilized with UV light and subsequently incubated in a culture medium favorable for microbial growth and inoculated with the fluorescent bacterium *Escherichia coli* transformed with the plasmid pGreenTir, which contains the gene that codes for the fluorescent protein. green (GFP). During an incubation period of 9 days, bacterial colonization on the different slide coatings was evaluated by counting fluorescent *E. coli* cells at different times (due to the presence of GFP), using an epifluorescence microscope (Leica DM5000 B) with 100× objective and fluorescence filter (excitation: 490 nm, emission: 515 nm).

FIG. 6. Results of biofilm formation by the colonization of cells of the *E. coli* GFP strain on surfaces of bio-active structures based on different types of polymers. The biofilm formation on different polymeric substrates is evaluated, in each case the control is evaluated, which corresponds only to the resin, the invention which is the resin mixed with ETA 0.01% to 0.1%, and as a comparison, it is shown an example of the respective resin mixed with the 0.1% zinc oxide antimicrobial compound. In FIG. 6-A the vinyl resin is studied, in FIG. 6-B the rubber resin is studied, in FIG. 6-C the polyurethane resin is studied and in FIG. 6-D the polyester resin is studied. In all the resins of the invention, there was a reduction in biofilm formation measured by the number of fluorescent cells adhered to the surface of the slide with the respective coating.

FIG. 7. Results on biofilm formation in marine environments. To determine the efficiency of the invention in environments such as the marine environment, where microbial biofilm formation can become a major problem, the marine bacterium *Cobetia* marina was used, which is a recognized model to study biofilm formation on surfaces, submerged in marine environments. Biofilm formation was measured using the crystal violet method. Likewise, and considering the biological factor of competition between species, in this case, it was considered to use live *Kocuria* cells, to evaluate if their presence limits the ability to form biofilms in the *Cobetia* marine bacterium. Biofilm formation by *Cobetia* marina is evaluated in seawater on surfaces coated with varnish, with varnish mixed with *Kocuria* sp bacteria at 0.1% w/v, and with varnish mixed with ETA extract at 0.1% w/v. The results show that both conditions of the invention significantly inhibit biofilm formation relative to the control.

DESCRIPTION OF THE INVENTION

The invention corresponds to a method of obtaining an extracellular extract produced by the growth in a liquid-solid two-phase culture medium of the marine bacterium degrading aromatic hydrocarbons *Kocuria* sp, to the extract produced, and to the use thereof to inhibit biofilm formation in aqueous environments. The applications of this use can be biomedical uses, including clinical uses, such as for industrial uses or even in domestic uses. In one embodiment, the extract of the invention can be incorporated into natural and synthetic polymeric resins while maintaining their activity, which makes it possible to generate devices or structures on whose surfaces the bacterial biofilm formation is inhibited. The extract of the invention has been called "ETA", which means Tense Active Extract, and the acronym will be used throughout the application and should be understood as the product of the invention.

The method of the invention is based on the culture of a bacterium isolated by the inventors and identified by its 16S rDNA as from the genus *Kocuria* without an assigned species and from the family of gram-positive Micrococaceae, phylum Actinobacteria. This bacterium was isolated from the marine environment as a degrader of aromatic hydrocarbons from petroleum. This particular *Kocuria* sp strain has Deposit number RGM2414 in the Chilean Collection of Microbial Genetic Resources (CChRGM), dated Dec. 20, 2017.

To obtain the extract of the invention, these bacteria, *Kocuria marina* sp, must be cultured in media for marine bacteria. Preferably, the culture medium used is a suitable medium for hydrocarbon-degrading heterotrophic marine bacteria, containing sterilized seawater at 80% (vol/vol) or double-distilled water containing NaCl between 3-5% w/vol), and a source of carbon chosen from sugars, organic acids and/or aromatic hydrocarbons in a concentration between 0.75 to 1.5% w/v. Additionally, a source of particulate inorganic material is added on a micrometer scale in an amount not greater than 0.01% (w/vol) to generate a solid-liquid two-phase culture. Bacteria grow until they reach the stationary phase of the culture.

The culture supernatant constitutes the microbial extract with properties that inhibit biofilm formation of and that comprises between 35 to 45% of palmitic acid; between 18 and 28% stearic acid and between 8 and 16% oleic acid.

Among the carbon sources that can be used are sugars such as glucose or organic acids such as citric acid compounds of the aromatic hydrocarbon type such as toluene, benzene, or aromatic molecules of the polycyclic type, such as biphenyl.

The culture medium must also contain inorganic salts such as magnesium sulfate; calcium chloride; monopotassium phosphate; di-ammonium hydrogen phosphate; potassium nitrate and ferric chloride and with a final pH between 6 and 8. Preferably, the medium comprises 0.2 g/L of magnesium sulfate; 0.02 g/L of calcium chloride; 1 g/L of monopotassium phosphate; 1 g/L of diammonium hydrogen phosphate; 1 g/L of potassium nitrate, and 0.05 g/L of ferric chloride, all these concentrations can vary by 20%. Incubation conditions for growth are shaking between 100 to 400 rpm, for 24-72 hours; temperature between 10° and 35° C.; and oxygen saturation between 10-21%.

Subsequently, the extract of the invention is obtained, which is preferably the culture supernatant. The processing of the extract depends on the application that it will have, for example for biomedical or biofilm inhibition applications in objects of direct contact with people or food, the extract is substantially cell-free and preferably completely cell-free. In this case, the extraction is based on the separation by centrifugation between 5,000 g to 8,000 g of cells, leaving a supernatant enriched in the extract, which is the bacterial extract of the invention. This obtained product can be subsequently concentrated by lyophilization or separated by chemical extraction, obtaining an extract in the form of a dry, cell-free powder.

For other embodiments such as inhibition of biofilm formation on submerged surfaces, such as boats or others, the extract of the invention may contain the cells of the marine bacterium *Kocuria* sp. Reducing the costs of the extracts of the invention, by avoiding a purification step, obtaining the same results in the inhibition of biofilm formation.

The product of the invention corresponds to a mixture of organic compounds of the fatty acid type, which provide emulsifying properties to the said mixture and inhibit biofilm formation. The inventors have determined that the extract of the invention can be mixed with different natural or synthetic polymeric resins to generate structures or bioactive covering surfaces that inhibit biofilm formation. Where these surfaces inhibit bacterial biofilm formation in environments immersed in liquid fluids that contain nutrients.

This property has been evaluated by determining biofilm formation using *Escherichia coli* as a model inoculum of biofilm formation, under different environmental conditions, such as, for example, immersion in human urine, distilled water, and seawater.

In one embodiment, the invention aims at polymeric structures that comprise the extract of the invention and that can be used for different purposes, from medical devices to paints or surface coatings, and that are capable of inhibiting microbial biofilm formation. The polymeric structures contain the extract of the invention (ETA), which can be obtained in a dry cell-free powder form. This ETA powder of the invention can be incorporated into natural or synthetic polymers, such as silicone, rubber, polyurethane, polyester, vinyl resin, epoxy resin, alkyd resin, or other resins, maintaining its activity so that it allows to form different polymeric structures with different uses that would have anti-biofilm formation properties. For example, structures such as silicone catheters or another polymer with anti-biofilm properties can be obtained, which allows that when immersed in complex environments, such as fluids that contain human urine and bacteria, these are not contaminated by bacteria, since these would affect their ability to form biofilms, without being able to colonize the structure of the catheter, keeping it safe and aseptic.

The extract of the invention, substantially cell-free, and preferably completely cell-free, makes it possible to obtain silicone or other resin structures suitable for medical use, such as catheters, probes, braces, implants, prosthetic hearts valves, joints, prosthetics, orthopedic implants, shunts, pacemakers and defibrillators, endotracheal tubes, hemodialysis/peritoneal dialysis devices, dental implants, and intravascular catheters.

On the other hand, the extract of the invention, which is substantially cell-free, makes it possible to obtain silicone or other resin structures suitable for the food industry, such as hoses, tapes, or chambers that are in contact with food or beverages.

In another embodiment, the extract of the invention makes it possible to obtain formulations of bioactive coatings or bioactive paints for surfaces submerged in fluids of biological origin, food, contaminated water, or seawater. In these cases, the extract does not need to be cell-free.

In another embodiment, the extract of the invention makes it possible to obtain formulations of additives for water, such example that for cooling reactors, to prevents biofilm formation in pipes, hoses, and/or metal or plastic containers. Depending on the subsequent use of the water, cell-free or non-cell-free extract can be used, where the extract is added to the water in a proportion between 0.01% and 10% of the water to be treated. Next, a preferred embodiment of the proposed invention is described, without limiting the technical variants that an expert in the field may incorporate or modify, and which are within the scope of the inventive concept that we claim in this application.

Examples

1. Obtaining the Cell-Free Extract of the Invention i) Fermentation or Bioprocess.

The process to obtain a cell-free extract from the strain of the present invention began by growing a pure inoculum of the strain of bacterium of marine origin degrading aromatic hydrocarbons *Kocuria* sp, deposit RGM2414 in a condition of two liquid-solid phases using a sterile culture medium containing 1.2% w/v of biphenyl as a carbon source and inorganic salts such as: 0.2 g/L of magnesium sulfate; 0.02 g/L of calcium chloride; 1 g/L of monopotassium phosphate; 1 g/L di-ammonium hydrogen phosphate; 1 g/L of potassium nitrate and 0.05 g/L of ferric chloride, all of them dissolved in distilled water and with a final pH of between 6 and 8. Seawater filtered to a size pore of 0.22 μm. The incubation conditions for growth were shaking at 300 rpm, for 48 hours; at a temperature of 25° C.; and oxygen saturation of 15%.

ii) Obtaining Cell-Free Extract from *Kocuria* sp Strain MM1A2AB.

The separation of the supernatant containing molecules of interest and the cells of the strain was carried out by means of centrifugation and filtration, where the centrifugation was carried out at 5,000 g for 15 minutes; where after discarding the settled phase, the supernatant was recovered, which was filtered by 0.22 μm cut-off filter; filtered supernatant is cell-free.

iii) Recovery of Cell-Free Extract as Solid

The cell-free supernatant obtained in the previous point, called ETA liquid extract, contains molecules generated by bacterial metabolism that give the anti-biofilm formation properties to the product of the invention. The obtained filtrate was subjected to lyophilization at −80° C. and 10 Mtorr, subsequently, sieving of the obtained powder was carried out, under agitation in a horizontal position, to remove impurities and salts. Finally, the sieved powder was dried at 40° C. for 24 hours.

2. Characterization of the Extract of the Invention

Chemical characterization was carried out on the cell-free extract produced by the bacterium *Kocuria* sp strain MM1A2AB, and it was determined that its composition corresponds to a mixture of organic molecules with the relative predominance of palmitic acid (C16: 0) with 39%; stearic acid (C18: 0) with 23% and Oleic acid (C18: 1) with 12% according to mass coupled gas chromatography (GC-MS) analysis. These results were complemented and corroborated in terms of qualitative analysis through Nuclear Magnetic Resonance analysis of protons (H-NMR) and carbon (C-NMR), in addition to Fourier Transform Infrared Spectroscopy (FTIR) analysis.

3. Preparation of Structures with Inhibitory Surfaces of Microbial Biofilms by Using the Extract of the Invention Different antimicrobial formulations based on polymers such as silicone and the cell-free supernatant extract of the strain of the invention, *Kocuria* (ETA) were developed to generate bio-active surfaces. According to the state of the art, as examples of comparison, formulations based on recognized antimicrobial agents were used such as: inorganic elements such as Silver (Ag), Zinc (Zn), and Copper (Cu), and organic compounds such as Saponin. To broaden the possible applications, ETA was incorporated with different polymers or resins to form structures with bioactive surfaces. The products used were vinyl resin, rubber, polyurethane, epoxy resin, alkyd resin, polyester, and alkyd resin. The incorporation of ETA was carried out by mixing and manual homogenization in a proportion of between 0.01% and 1% (w/vol). The polymerization was carried out by drying at room temperature of 20° C. for at least 72 hours. According to the application, molds were manufactured to generate tubular structures of the "catheters" type or by depositing them on a glass surface to generate a coating or "coating". FIG. 1 shows the process of mixing and manufacturing structures based on ETA. FIG. 1-D shows a tubular structure obtained by using a glass mold and defined as a "catheter". FIG. 1-E shows the formation of a film deposited on a slide and defined as a "coating" or "coating".

For the evaluation tests, the structures with bio-active surfaces made based on different formulations with the cell-free bacterial extract of the present invention (ETA), were subjected to sterilization by autoclaving at 121° C. and 1 PSI for 15 minutes, and also the surfaces were treated with ultraviolet light for 5 minutes.

4. Bacterial Biofilms Formation and Viability in the Presence of Structures with Bio-Active Surfaces Containing ETA The state of the art and the technique indicates that biofilms formation is essential for the survival of microorganisms in a given environment. Forming biofilms creates a protective environment where microorganisms find nutrients, can reproduce, colonize, and resist the effect of antimicrobial agents. To evaluate the usefulness of the structures based on the extract produced by the present invention (ETA), the effect of the inhibition of biofilm formation and the viability of bacteria in the presence of structures with bio-active surfaces was evaluated. For this, strains of bacteria and conditions were used that allow checking the efficiency of the structures under conditions according to different applications in which they can be used.

4.1. Evaluation of Biofilm Formation and Bacterial Viability in Catheter-Like Structures and Coatings Based on ETA.

Figure 2:
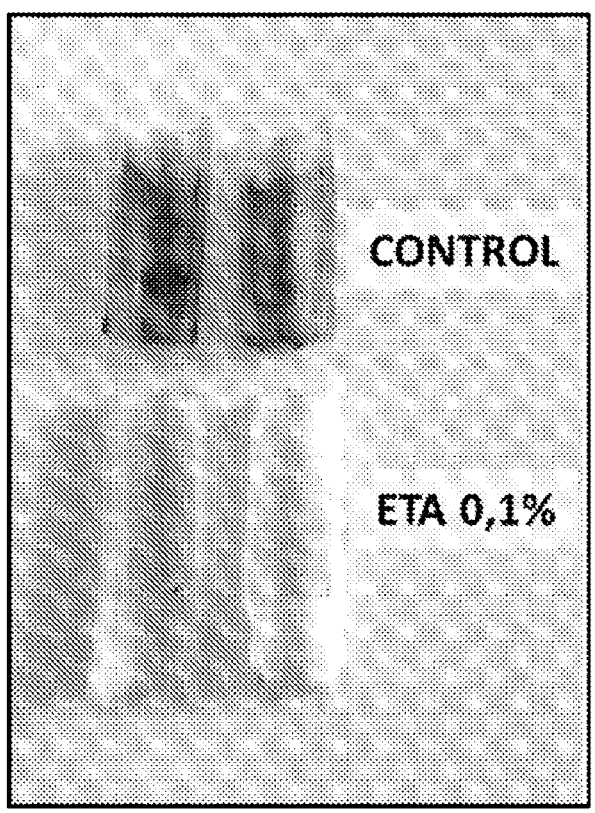
Figure 3:
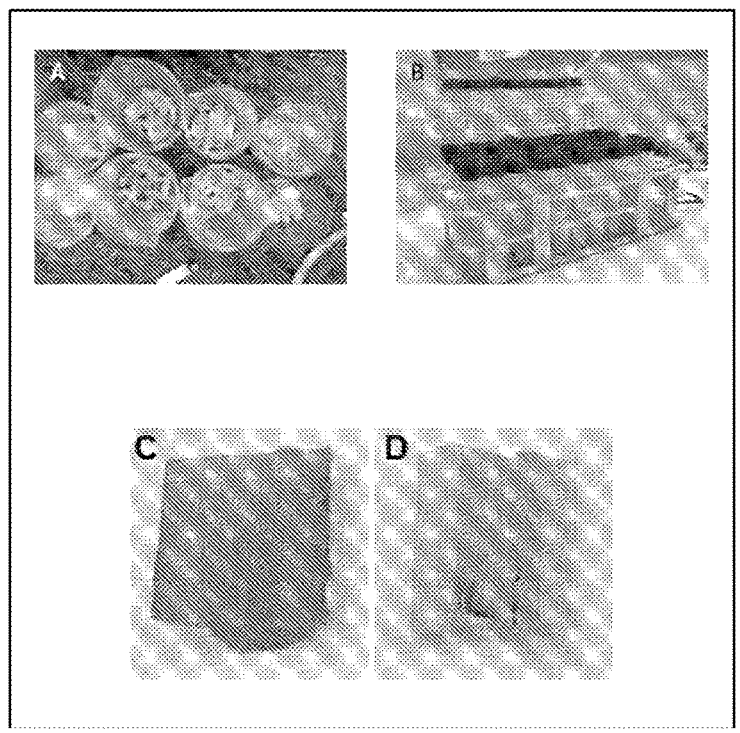

The results of biofilm formation in the "catheters" are shown in FIGS. 2 and 3. For their part, the viability tests of bacteria in the urine environment with the "catheters" are analyzed in FIG. 4.

4.1.1. Biofilm Formation in Catheters Formed with ETA.

FIG. 2 shows a biofilm formation assay with *E. coli* using "catheters" formulated based on ATE and its control. The test was carried out using the crystal violet staining technique and it is possible to verify the biofilm formation by an increase in the intensity of color in the "catheters" subjected to a liquid environment containing a determined number of bacteria for at least 48 hours. It is appreciated that the silicone "catheters" containing ETA (0.01% to 0.1% w/vol.) Immersed in a Luria Bertani culture medium containing cells of the *E. coli* bacteria, and incubated at 37° C. do not show violet crystal staining, while the control "catheters" without ETA immersed in the same Luria Bertani culture medium and incubated at 37° C. containing cells of the bacterium *E. coli*, they present an intense color due to biofilm formation.

Urine has a chemical composition and physical and chemical characteristics that can favor the proliferation of pathogens. To evaluate the usefulness of the structures based on the extract produced by the present ETA invention, the condition of biofilm formation in urinary catheters was simulated, for which infectious disease model bacteria were used in a urine environment, that is, bacteria of the genus that are recognized for generating urinary tract infections in patients who are catheterized through the urinary tract. In this case, the *E. coli* bacteria were used and, in particular, for a viability evaluation, staining was used that allows, through the use of fluorescence microscopic techniques, to determine the viability of bacteria in a sample. The method makes it possible to determine the number of living and dead bacteria by microscopic observation. In turn, the crystal violet staining technique was used to determine the presence of biofilms on surfaces. FIG. 3-A shows different structures of the "catheters" type formulated based on different components and the ETA of the *Kocuria* strain of the present invention. FIG. 3-B shows the urine immersion tests containing *E. coli* bacteria cells, which were incubated at 37° C. FIGS. 3 C and D show "catheters" obtained after 10 days and stained by the crystal violet method to see the biofilm formation. Image C shows the catheter surface with greater staining (dark) due to the formation of *E. coli* biofilms in urine. Image D shows the surface of a catheter manufactured using ETA and silicone (clear image with less staining) where it is possible to appreciate less biofilm formation.

4.1.2. Bacterial Viability in the Condition of Exposure to Catheters Made with ETA.

Figure 4A:
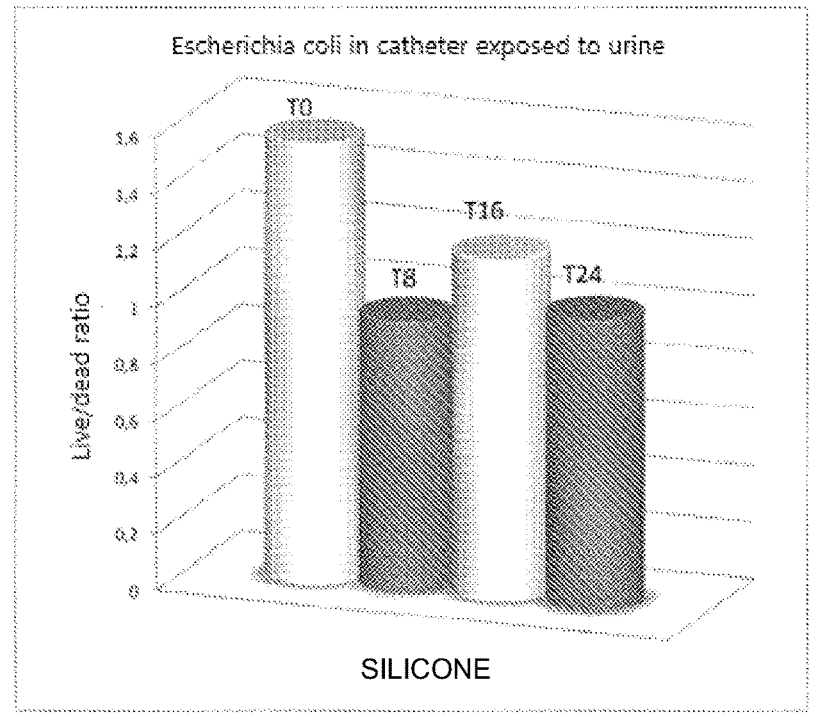
Figure 4B:
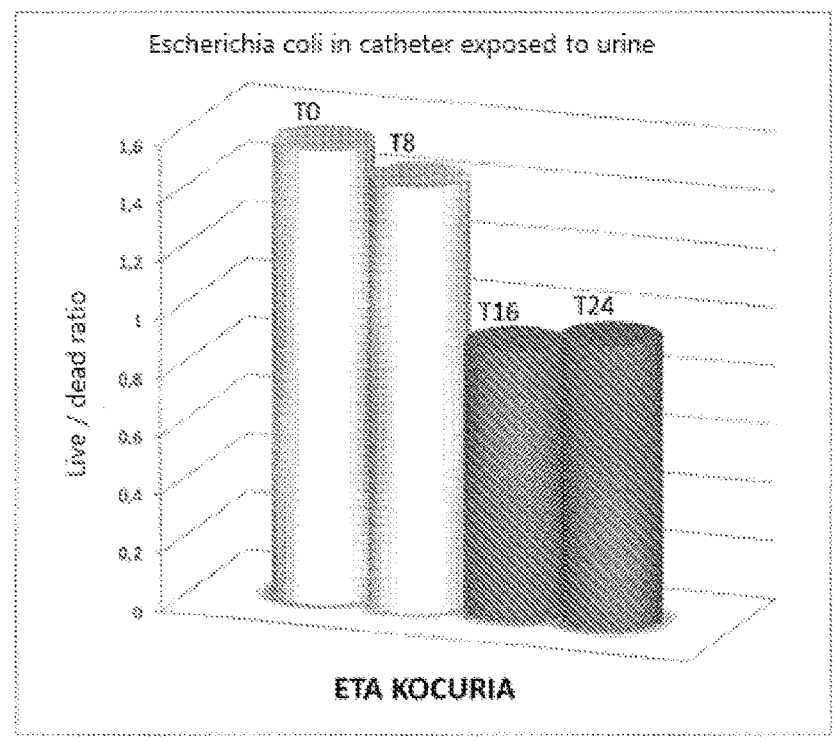
Figure 4C:
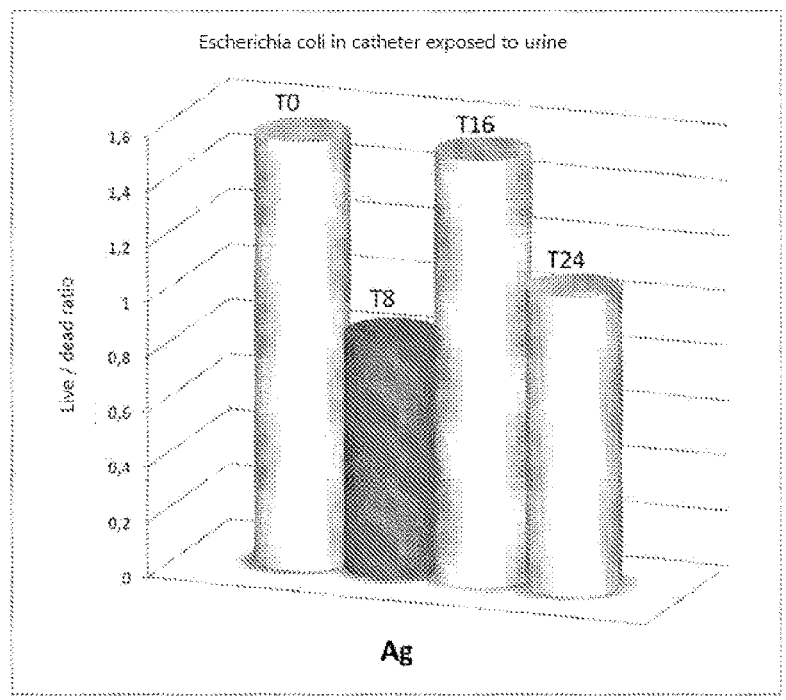

The results of the viability of *E. coli* in urine in time (0, 8, 16, and 24 hours) with some of the different "catheters" made based on the silicone polymer according to Table 1 are shown in the series of FIG. 4. FIG. 4-A corresponds to the control condition where the "catheter" was manufactured based on only silicone, without incorporating any antimicrobial agent or ETA. As the column chart shows the proportion of live/dead cells is around the value 1 at time 24 hours, which shows a reduction in time due to the urine environment. In relation to the structures made with the *Kocuria* ETA of the present invention, it is possible to appreciate that, in relation to the control (this is silicone without antimicrobial agents), there is an effect after 16 hours and 24 hours (FIG. 4-B). These results show that the incorporation of the ETA of the invention allows to significantly reduce biofilm formation in silicone exposed to urine, in comparison with another compound known for its biocidal properties, such as silver Ag particles, which do not inhibit the growth of *E. coli* in urine (FIG. 4-C).

4.2. Evaluation of Biofilm Formation on Coatings Made with ETA.

Figure 5:
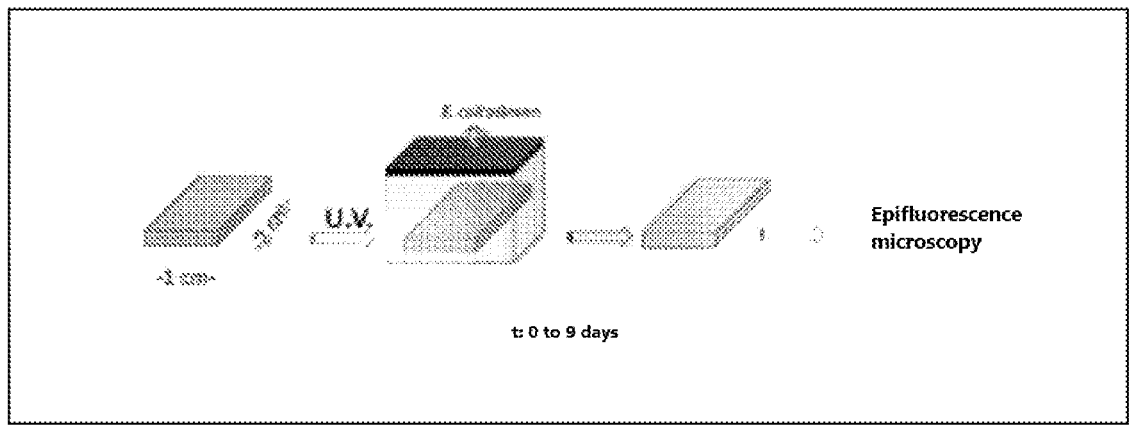
Figure 6A:
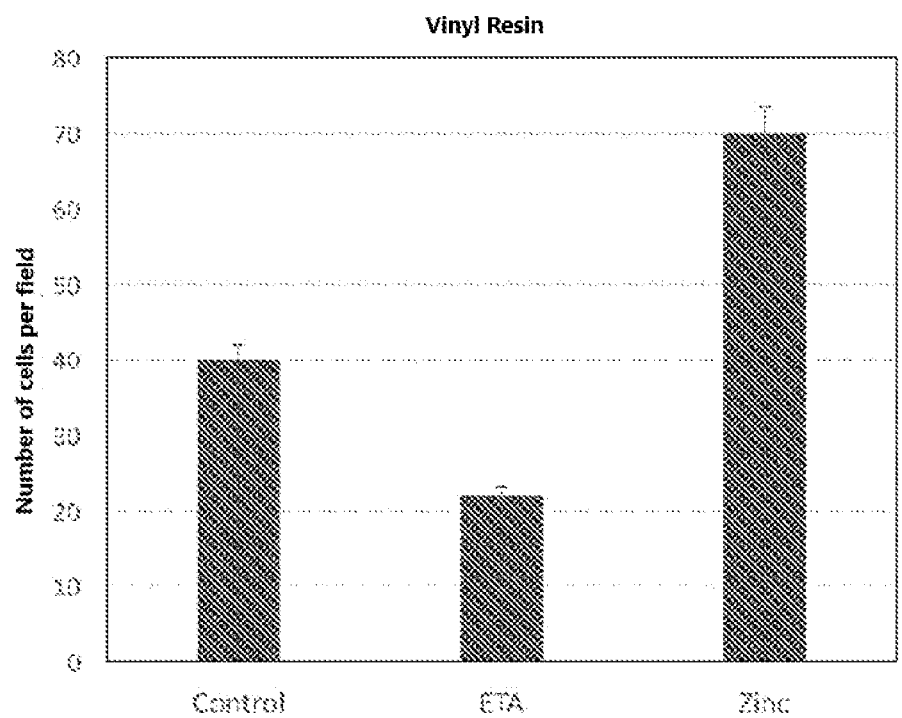
Figure 6B:
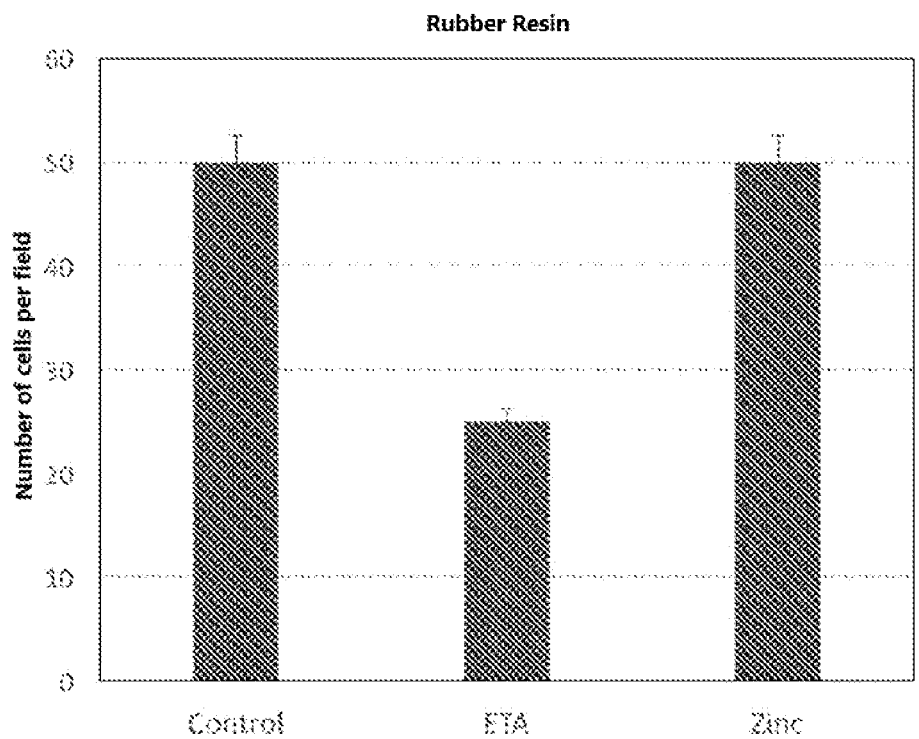
Figure 6C:
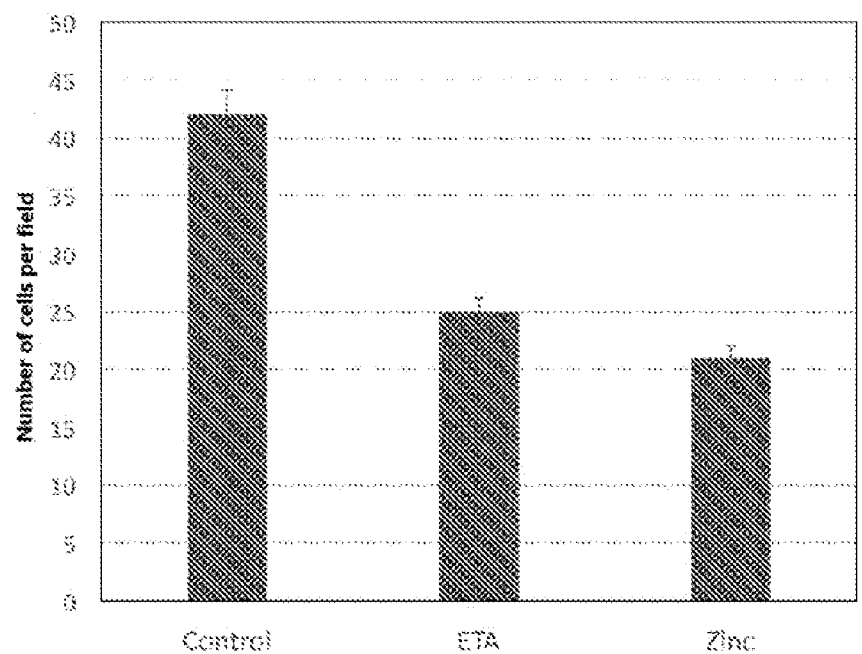
Figure 6D:
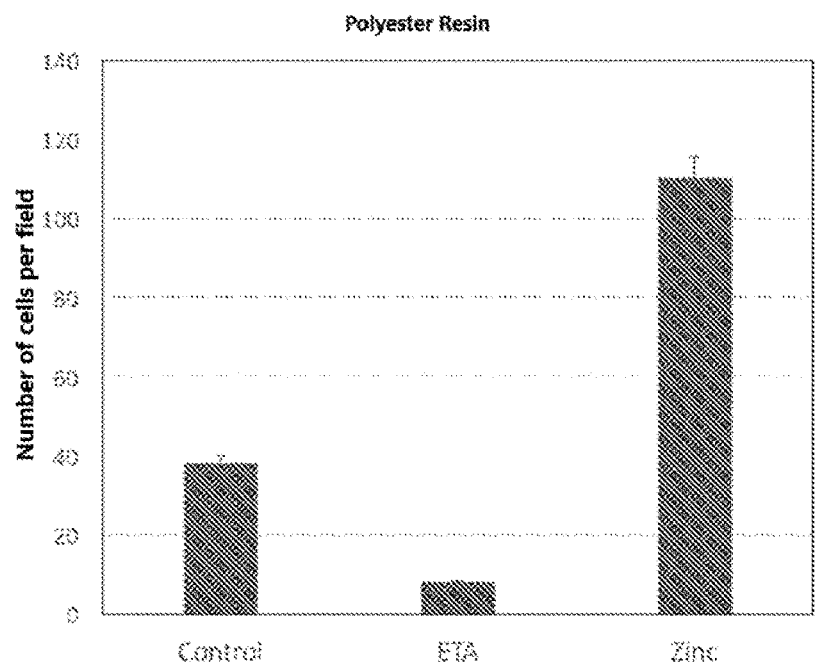

For this, different surfaces of the structures were manufactured using synthetic or natural polymers. The resins used were: 1.—Vinyl Resin; 2.—Rubber; 3.—Epoxy Resin; 4.—Polyurethane Resin; 5.—Alkyd Resin; 6.—Polyester Resin. In each case, the control, which comprises only the resin, the resin mixed with the ETA extract of the invention in a concentration of 0.1% (w/vol.) was evaluated. And the resin mixed with another biocidal compound, such as zinc oxide (ZnO) in a concentration of 0.1% (w/vol.). With each mixture, a millimeter film was generated on a glass slide. The different slides containing the respective films of the coatings were exposed to ultraviolet light for 15 minutes in order to sterilize them. They were then exposed by immersion in a culture medium to the presence of a fluorescent *Escherichia coli* bacteria containing the plasmid pGreenTir, which contains the GFP gene. The test is outlined in FIG. 5.

FIG. 6 shows the results of the biofilm formation of the *E. coli* GFP strain on the surfaces of bioactive structures of the invention based on different types of polymers or resins. The results are expressed as the number of fluorescent bacteria per field, using an epifluorescence microscope (Leica DM5000 B). As can be seen concerning the control, the incorporation of ETA in the different coatings managed to reduce the number of bacteria absorbed to the surface. And in most cases, ETA performed better than Zinc (Zinc oxide). From In this way, it is possible to conclude that incorporating ETA in a coating or coating with different polymeric materials, such as vinyl, rubber, polyurethane, and polyester, for example makes it possible to inhibit the development of biofilms.

4.3. Evaluation of the Inhibition Capacity of Biofilm Formation in Submerged Marine Environments.

Submerged marine surfaces are normally affected by the microbial biofilm formation that start the microfouling process and then finish in the macrofouling. This situation is negative when the affected areas correspond to materials or production facilities. For these reasons, numerous strategies to prevent the formation of micro and macro fouling have been developed, the most effective being those that use paints or coatings based on heavy metals. Unfortunately, these solutions are toxic for native species and represent environmental contamination, which is why there is currently a need to look for new alternatives.

Figure 7:
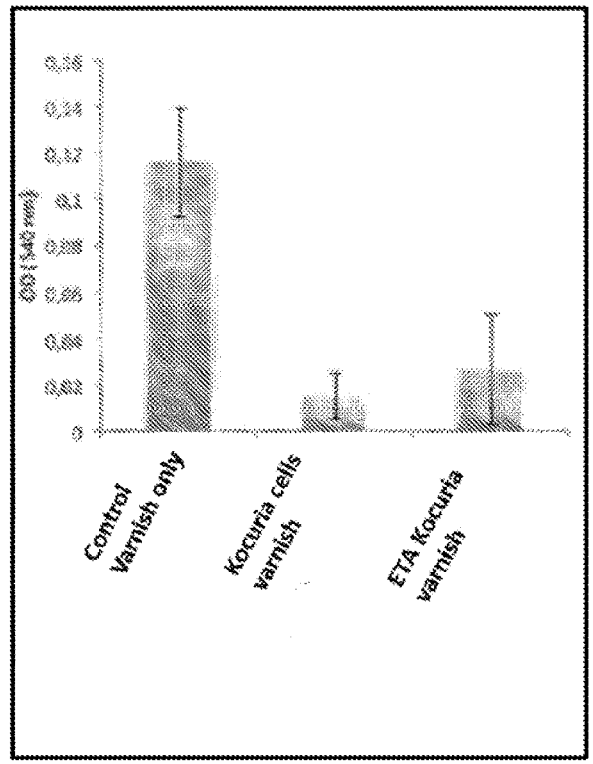

It is in this scenario that the ETA generated by *Kocuria* of the present invention was evaluated to see if its incorporation allows the inhibition of microbial biofilms in the marine environment. The trial used the *Cobetia* marina strain as a model for marine biofilm-forming bacteria in the marine environment. The literature points to this microorganism as a model for studying biofilm formation. For the test, surfaces were prepared with a commercial varnish coverage containing a *Kocuria* culture, that is, ETA supernatant and the cells present (*Kocuria* Varnish) at a concentration of 0.1% (w/vol) and the same varnish containing only the culture supernatant (ETA Varnish) in a proportion of 0.1% (w/vol). The tests were carried out by immersing the surfaces in seawater containing at least $1\times10\,6$ cells of *Cobetia* marina for one week. After this time, the exposed *Cobetia* marine bacteria were tested for biofilm formation capacity by crystal violet staining and microscopic visualization. The results are shown in FIG. 7 and indicate that the ETA Varnish and the *Kocuria* Varnish of the present invention, inhibit biofilm formation of *Cobetia* marina in a seawater condition.

The invention claimed is:

1. A method of producing a bacterial extract that inhibits microbial biofilm formation, comprising:
    a) culturing a marine bacterium *Kocuria* sp strain, MM1A2AB Deposit RGM2414 strain in a sterile culture medium for marine bacteria comprising: between 0.75 to 1.5% w/v of a single carbon source selected from a sugar, an organic acid and an aromatic hydrocarbon and 80% (v/v) of at least one liquid selected from the group consisting of sterilized seawater and double-distilled water, wherein the at least one liquid selected from the group consisting of sterilized water and double-distilled water comprises NaCl between 3-5% w/v, so as to obtain a culture, and
    b) obtaining a supernatant of the culture obtained in a), wherein the supernatant corresponds to the bacterial extract, and comprises between 35 to 45% of palmitic acid, between 18 and 28% of stearic acid, and between 8 and 16% of oleic acid.

2. The method according to claim 1, wherein the supernatant is separated by centrifugation between 5,000 g to 8,000 g and by filtration through a pore size of 0.25 pm and the supernatant is substantially free of cells.

3. The method according to claim 2, wherein the substantially cell-free supernatant is lyophilized at −80° C. and 10 Mtorr for at least 24 hours.

4. The method according to claim 1, wherein the sterile culture medium used in a) also comprises: 0.2 g/L of magnesium sulfate; 0.02 g/L of calcium chloride; 1 g/L of monopotassium phosphate; 1 g/L of diammonium hydrogen phosphate; 1 g/L of potassium nitrate and 0.05 g/L of ferric chloride, wherein the concentrations of the magnesium sulfate, the calcium chloride, the monopotassium phosphate, the diammonium hydrogen phosphate, the potassium nitrate, and the ferric chloride can each vary by up to 20%.

5. The method according to claim 1, wherein a) is carried out under; shaking between 100 to 400 rpm, for 24-72 hours under pH conditions between 6 and 8; a temperature between 10° and 35° C.; and an oxygen saturation between 10-21%.

6. The method according to claim 1, wherein the carbon source is selected from the sugar and the organic acid.

7. The method according to claim 1, wherein the carbon source is the aromatic hydrocarbon.

* * * * *